(12) United States Patent
Peng et al.

(10) Patent No.: US 8,829,213 B2
(45) Date of Patent: Sep. 9, 2014

(54) LIVER X RECEPTOR AGONISTS

(75) Inventors: Dacheng Peng, Chicago, IL (US); John Kokontis, Chicago, IL (US); Richard Hiipakka, Chicago, IL (US); Shutsung Liao, Chicago, IL (US)

(73) Assignee: The University of Chicago, Chicago, IL (US)

( * ) Notice: Subject to any disclaimer, the term of this patent is extended or adjusted under 35 U.S.C. 154(b) by 202 days.

(21) Appl. No.: 12/846,326

(22) Filed: Jul. 29, 2010

(65) Prior Publication Data

US 2011/0059932 A1    Mar. 10, 2011

Related U.S. Application Data

(60) Provisional application No. 61/229,386, filed on Jul. 29, 2009.

(51) Int. Cl.
*C07J 9/00* (2006.01)

(52) U.S. Cl.
CPC ... *C07J 9/00* (2013.01); *C07J 9/005* (2013.01)
USPC .......................................................... 552/551

(58) Field of Classification Search
USPC .......................................................... 552/551
See application file for complete search history.

(56) References Cited

U.S. PATENT DOCUMENTS

| | | | |
|---|---|---|---|
| 2,698,853 A | 1/1955 | Wildi | |
| 3,784,598 A | 1/1974 | Iseli et al. | |
| 3,887,545 A | 6/1975 | Iacobelli et al. | |
| 3,925,480 A | 12/1975 | Thal et al. | |
| 3,963,765 A | 6/1976 | Mazur et al. | |
| 4,006,172 A | 2/1977 | Salmond | |
| 4,125,544 A | 11/1978 | Dygos | |
| 4,193,930 A | 3/1980 | Chorvat | |
| 4,304,726 A | 12/1981 | Arakawa et al. | |
| 4,639,420 A | 1/1987 | Schaffner | |
| 4,917,898 A | 4/1990 | Angelico et al. | |
| 5,332,857 A | 7/1994 | McCarthy et al. | |
| 5,362,891 A | 11/1994 | Bonaldi et al. | |
| 5,424,463 A | 6/1995 | Lardy et al. | |
| 5,466,815 A | 11/1995 | Enhsen et al. | |
| 5,482,935 A | 1/1996 | Adelman et al. | |
| 5,508,453 A | 4/1996 | Arosio et al. | |
| 5,562,910 A | 10/1996 | Daynes et al. | |
| 5,583,239 A | 12/1996 | Regen | |
| 5,639,744 A | 6/1997 | Marchi et al. | |
| 6,060,465 A | 5/2000 | Miljkovic et al. | |
| 6,369,247 B1 | 4/2002 | Miller et al. | |
| 6,465,258 B1 | 10/2002 | Shan et al. | |
| 6,639,078 B1 | 10/2003 | Haffner et al. | |
| 6,645,955 B1 | 11/2003 | Liao et al. | |
| 2002/0107233 A1 | 8/2002 | Liao et al. | |
| 2002/0193357 A1 | 12/2002 | Song et al. | |
| 2003/0139385 A1 | 7/2003 | Song et al. | |
| 2004/0014734 A1 | 1/2004 | Song et al. | |
| 2007/0032464 A1 | 2/2007 | Liao et al. | |

FOREIGN PATENT DOCUMENTS

| | | |
|---|---|---|
| CN | 1100729 | 3/1995 |
| EP | 0562 849 | 9/1993 |
| GB | 1405 818 | 9/1975 |
| GB | 2009 180 | 6/1979 |
| JP | 4169597 | 6/1992 |
| JP | 2002-030096 | 1/2002 |
| WO | WO 94/02503 | 2/1994 |
| WO | WO 98/32444 | 7/1998 |
| WO | WO 00/66611 | 11/2000 |
| WO | WO 02/062302 | 8/2002 |
| WO | WO 02/090375 | * 11/2002 |
| WO | WO 03/039480 | 5/2003 |
| WO | WO 03/086303 | 10/2003 |

OTHER PUBLICATIONS

Shen Zheng-Wu et al., "Study on the Syntheses of Brassinolide and Related Compounds. Part 14. Highly Stereoselective Construction of the Side-chain of Brassinosteroids utilizing the beta-alkylative 1,3-Carbonyl Transposition of teh Steroidal 22-En-24-one." J. Chem. Soc., Perkin Trans. 1, pp. 1765-1767, 1990.*

Song C. et al., "Effects of Selective Liver X Receptor Agonist on Atherosclerosis Progression and Regression of Apoe Knock-Out Mice" Circulation, American Heart Association, Dallas, TX, US, vol. 104, No. 17, Oct. 23, 2001, p. II329, XP009016063, ISSN: 0009-7322.

Sparks D. L. et al., "Link Between Heart Disease, Cholesterol, and Alzheimer's Disease: a Review" Microscopy Research and Technique, Aug. 15, 2000, vol. 50, No. 4, pp. 287-290, XP002462914, ISSN: 1059-910X.

Song C. et al., "Selective Activation of Liver X Receptor Alpha by 6Alpha-Hydroxy Bile Acids and Analogs" Steroids, Elsevier Science Publishers, New York, NY, US, vol. 65, No. 8, 2000, pp. 423-427, XP000952749, ISSN: 0039-128X.

Song C. et al., "Hypolipidemic Effects of Selective Liver X Receptor Alpha Agonists" Steroids, Butterworth-Heinemann, Stoneham, MA, US, vol. 66, No. 9, Sep. 2001, pp. 673-681, XP004304415, ISSN: 0039-128X.

(Continued)

*Primary Examiner* — Barbara P Badio
(74) *Attorney, Agent, or Firm* — Cesari and McKenna, LLP

(57) ABSTRACT

Compounds of formula (I):

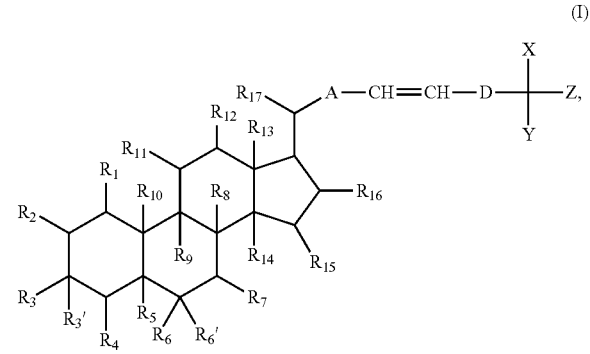

in which $R_1$, $R_2$, $R_3$, $R_{3'}$, $R_4$, $R_5$, $R_6$, $R_{6'}$, $R_7$, $R_8$, $R_9$, $R_{10}$, $R_{11}$, $R_{12}$, $R_{13}$, $R_{14}$, $R_{15}$, $R_{16}$, $R_{17}$, A, D, X, Y, and Z are defined in the specification. Also disclosed is a method of using one of the compounds to lower the blood cholesterol level and treat cancer, atherosclerosis, diabetes, Alzheimer's disease, and corneal arcus.

1 Claim, No Drawings

(56) References Cited

OTHER PUBLICATIONS

Laffitte B.A. et al., "LXRS Control Lipid-Inducible Expression of the Apolipoprotein E Gene in Macrophages and Adipocytes" Proceedings of the National Academy of Sciences of USA, National Academy of Science, Washington, DC, US, vol. 98, No. 2, Jan. 16, 2001, pp. 507-512, XP-001097136, ISSN: 0027-8424.
Cohen-Solal et al. "Effects of hyodeoxycholic acid and alpha-hyocholic acid, two 6 alpha-hydroxylated bile acids, on cholesterol and bile acid metabolism in the hamster." Biochimica et biophyusica Acta, vol. 1257, pp. 189-197, 1995.
Angelico et al., "Dissolution of Human Cholesterol Gallstones in Bile Salt/Lecithin Mixtures: Effect of Bile Salt Hydrophobicity and Various pHs", Scandinavian Journal of Gasteroenterology 30:1178-1185, 1995.
Bleau et al. "Cholesterol sulfate, Occurrence and possible biological function as an amphipathic lipid in the membrane of the human erythrocyte." Biochimica et Biophysica Acta, vol. 352(1), pp. 1-9, (1974).
Ajay Chawla et al., "Nuclear Receptors and Lipid Physiology: Open The X-Files", Science, vol. 294, pp. 1866-1870 (Nov. 30, 2001).
Cohen et al., "The preparation of bile acid amides and oxazolines. II. The synthesis of the amides and oxazolines of ursodeoxycholic acid, deoxycholic acid, hyodeoxycholic acid and cholic acid", Steroids, vol. 40, No. 6, pp. 701-711 (Dec. 1982).
Coleman et al., "Synthesis and Characterization of Novel Analogs of Conjugated Bile Acids Containing Reversed Amide Bonds", Journal of Lipid Research 36:901-910, 1995.
Dusza et al., "A Fusion Method for Preparation of Steroid Sulfates," Steroids p. 317-323 (1985).
Dusza et al., "The Preparation of Estradiol-17β Sulfates with Triethylamine-Sulfur Trioxide," Steroids p. 303-315 (1985).
Adomo Fini et al., "Quantitative Structure-Antimicrobial Activity Relationship in 5β-Cholanyl-24-benzylamine Derivatives", Journal of Pharmaceutical Sciences, vol. 79, No. 7, pp. 603-605 (Jul. 1990).
Charles Freudenreich, et al., "Design of Inhibitors from the Three-Dimensional Structure of Alcohol Dehydrogenase, Chemical Synthesis and Enzymatic Properties", J. Am. Chem. Soc., pp. 3344-3353, (1984).
Xuan Fu et al., "27-Hydroxycholesterol Is an Endogenous Ligand for Liver X Receptor in Cholesterol-loaded Cells", The Journal of Biological Chemistry, Vo. 276, No. 42, pp. 38378-38387 (2001).
Josef E. Herz, et al., "Fluorinated Sterols. Part II: 26,27—Polyfluorinated Desmosterols", Journal of Fluorine Chemistry, vol. 8, pp. 209-222 (1976)
Mohammed N. Iqbal, et al., "Bile Acids. LXXXI. Synthesis and structural assignment of E/Z isomers of substituted methyl hydroxy-5β-cholest-24-en-26-oates", Steroids, vol. 56, pp. 505-512 (Oct. 1991).
Janowski et al., "Structural Requirements of Ligands for the Oxysterol Liver X Receptors LXRα and LXRβ", Proc. Natl. Acad. Sci. vol. 96, pp. 266-271, (Jan. 1999).
Kim et al., "Inhibitors of Sterol Synthesis. Chemical Synthesis, Structure, and Biological Activities of (25R)-3β,26-dihydroxy-5α-cholest-8(14)-en-15-one, a Metabolite of 3β-hydroxy-5α-cholest-8(14)-en-15-one", Journal of Lipid Research 30:247-261, 1989.
Naoyuki Koizumi, et al., Synthesis of [25R]—and [25S]-25,26-Dihydroxyvitamin D31, Tetrahedron Letters, No. 32, pp. 2899-2902 (1978).
Kornel et al., "Studies on Steroid Conjugates: II Chemical Synthesis and Characterization of Sodium Cortisol-21-Sulfate and Sodium Tetrahydrocortisol-3, 21-Disulfate," Steroids. p. 67-75 (1964).
A. Kuritzkes, et al., "3-epi-Uzarigenin und 3-epi-17I-Uzarigenin", Helvetica Chimica Acta, vol. 62, pp. 1502-1515 (1959).
Kurosawa et al., "Synthesis of 3α, 7α, 12α-trihydroxy-and 3I, 7I-dihydroxy-59-cholestan-26-oic Acids by the Use of 9-ketosulfoxide", Steroids 60:439-444, 1995.
Yvonne Lange, et al., "Cholesterol Movement in Niemann-Pick Type C Cells and in Cells Treated with Amphiphiles", The Journal of Biological Chemistry, vol. 275, No. 23, pp. 17468-17475, (Jun. 9, 2000).

Dieter Leibfritz, et al., "Nuclear Magnetic Resonance Spectroscopy. Carbon-13 Spectra of Cholic Acids and Hydrocarbons Included in Sodium Desoxycholate Solutions", Journal of American Chemical Society, vol. 95, No. 14, pp. 4996-5003 (Jul. 11, 1973)
Li et al., "Sterol Synthesis. Preparation and Characterization of Fluorinated and Deuterated Analogs of Oxygenated Derivatives of Cholesterol", Chemistry and Physics of Lipids 99:33-71, 1999.
Nambara et al., "Preparation of Specific Antiserum to Estriol 3-Sulfate 16-Glucuronide," Journal of Steroid Biochemistry, 21: p. 199-203 (1984).
S.H. Mujtaba Naqvi, "Chemical Synthesis and Mass Spectrometric Characterization of Some C-27 Steroids", Steroids, vol. 22, pp. 285-290 (1973).
J. Polonia, et al., "Die Konstitution des Xysmalogenins", Helvetica Chimica Acta, vol. 42, pp. 1437-1447 (1959).
Roda et al., "Synthesis and Phsicochemical, Biological, and Pharmacological Properties of New Bile Acids Amidated with Cyclic Amino Acids", J. Med. Chem. 39:2270-2276, 1996.
Ruelle et al., "The Mobile Order Solubility Equation Applied to Polyfunctional Molecules: The Non-hydroxysteroids in Aqueous and Non Aqueous solvents", International Journal of Pharmaceutics 157:219-232, 1997.
Ching Song et al., "Auto-oxidized cholesterol sulfates are antagonistic ligands of liver X receptors: implications for the development and treatment of atherosclerosis", Steroids, vol. 66, pp. 473-479 (2001).
Song et al., "Cholestenioc Acid Is a naturally Occurring Ligand for Liver X Receptor ∀," Endocrinology, 141: p. 4180-4184 (2000).
Song et al., "Ubiquitous Receptor: A Receptor that Modulates Gene Activation by Retinoic Acid and Thyroid Hormone Receptors", Proc. Natl. Acad. Sci. 91:10809-10813, 1994.
Song et al., "Ubiquitous Receptor: Structures, Immunocytochemical Localization, and Modulation of Gene Activation by Receptors for Retinoic Acids and Thyroid Hormones", Annals of the New York Academy of Sciences 761:38-49, 1995.
Sweeny et al., "Metabolism of 5-fluorouracil to an N-cholyl-2-fluoro-9-alanine conjugate: Previously Unrecognized Role for Bile Acids in Drug Conjugation", Proc. Natl. Acad. Sci. 84:5439-5443, 1987.
Summerfield et al., "Identification of Bile Acids in the Serum and Urine in Cholestasis", Biochem. J. 154:507-516, 1976.
C Tamm, et al., "Umwandlung von Cardenoliden durch Mikroorganismen. III. Umsetzung von Aglykonen und Glykosiden mit Fusarium lini", Helvetica Chimica Acta, vol. 42, pp. 239-259 (1959).
Tanaka et al., "Specific Antisera for the Radioimmunoassay of Estradiol-3-Sulfate," Journal of Steroid Biochemistry, 22: p. 285-288 (1985).
R. Tschesche, et al., "Uber pflanzliche Herzgifte, XIX. Mitteil., Die Glykoside der Uzara-Wurzel", Chemische Berichte, vol. 85, pp. 1042-1053 (1952).
Varma et al., "Synthesis and C-25 Chirality of 26-Hydroxycholesterols", The Journal of Organic Chemistry 40:3680-3686, 1975.
Wei et al., "Modulation of Hormone-dependent Glucocorticoid Receptor Function Using a Tetracycline-regulated Expression System", J. Steroid Biochem. Molec. Biol. 64:1-12, 1998.
Michael W. Whitehouse et al., "Catabolism in vitro of cholesterol: some comparative aspects", Arch. Biochem. Biophys., 98, pp. 305-311 (1962).
Xia et al., "Synthesis of N-Substituted 3-OXO-17-Carboxamide-4-AZA-5I-Androstanes and the Tautomerism of 3-OXO-4-AZA-5-Androstenes", Heterocycles 47:703-716, 1998.
Stephen A. Ziller, Jr., et al., "Bile Acids. XXV. Allochenodeoxycholic Acid, A Metabolite of 5α-Cholestan-3β-OL in the Hyperthyroid Rat", The Journal of Biological Chemistry, vol. 243, pp. 5280-5288 (1968)
Bleau G. et al., "Cholesterol Sulfate, Occurrence and possible biological function as an amphipathic lipid in the membrane of the human erythrocyte", Biochim. Ciophys, Acta, vol. 352, No. 1, pp. 1-9, Database HPCAPLUS, AN 1974:461503 (Jan. 1974).
Susan Budavari, Editor, The Merck Index, An Encyclopedia of Chemicals, Drugs, and Biologicals, 11th Edition, published by Merck & Co., Inc., pp. 396, 574, 1225-1226 (1989).

(56) References Cited

OTHER PUBLICATIONS

Edwards et al., "BAREing it all: the adoption of LXR and FXR and their roles in lipid homeostasis", *J. Lipid Res.*, vol. 43, pp. 2-12 (2002).
Hofmann, "The Continuing Importance of Bile Acids in Liver and Intestinal Disease", *Arch. Intern. Med.*, vol. 159, pp. 2647-2658 (1999).
Makishima et al., "Identification of a Nuclear Receptor for Bile Acids", *Science*, vol. 284, pp. 362-365 (1999).
Roda et al., "New 6-substituted bile acids: physico-chemical and biological properties of 6α-methyl ursodeoxycholic acid and 6α-methyl-7-epicholic acid", *J. Lipid Res.*, vol. 35, pp. 2268-2279 (1994).
Roda et al., "Structure-Activity Relationship Studies on Natural and Synthetic Bile Acid Analogs", *Dig. Dis. and Sci.*, vol. 34, No. 12, pp. 24S-35S (1989).
Runong Wang et al., "Chemical Product Manual", the third version, Pharmaceuticals, Chemical Industry Publishing House, pp. 740 (Jan. 1999).
Bergmann et al., "Contribution to the study of marine products. XXXI. Palysterol and other lipid components of sea anemones", *Journal of Organic Chemistry*, 16:1337-1344 (1951).
Boto et al., "Tandem b-Fragmentation-hydrogen Abstraction Reaction of Alkoxy Radicals in Steroid Systems", *Journal of Organic Chemistry*, 62(9):2975-2981 (1997).
Database Beilstein 'Online!, *Beilstein Institute for Organic Chemistry*, BRN 1274114, XP002284519.
Database Beilstein 'Online!, Beilstein Institute for Organic Chemistry, Citation No. 575886, BRN 45135, 41670, XP002284520.
Database Beilstein 'Online!, Beilstein Institute for Organic Chemistry, BRN 1629436, XP002284521.
Database Beilstein 'Online!, Beilstein Institute for Organic Chemistry, BRN 1355280, XP002284522.
Database Beilstein 'Online!, Beilstein Institute for Organic Chemistry, BRN 41863, XP002284523.
Database Beilstein 'Online!, Beilstein Institute for Organic Chemistry, BRN 39425, XP002284524.
Database Beilstein 'Online!, Beilstein Institute for Organic Chemistry, BRN 1272804, XP002284525.
Database Beilstein 'Online!, Beilstein Institute for Organic Chemistry, BRN 4723631, XP002284526.
Database Beilstein 'Online!, Beilstein Institute for Organic Chemistry, BRN 6282221, XP002284527.
Database Beilstein 'Online!, Beilstein Institute for Organic Chemistry, BRN 6781196, XP002284528.
Database Beilstein 'Online!, Beilstein Institute for Organic Chemistry, BRN 7545061, XP002284529.
Database Beilstein 'Online!, Beilstein Institute for Organic Chemistry, BRN 7950623, XP002284530.
Database Beilstein 'Online!, Beilstein Institute for Organic Chemistry, BRN 7954188, XP002284531.
Database Beilstein 'Online!, Beilstein Institute for Organic Chemistry, BRN 2017533, XP002284532.
Database Beilstein 'Online!, Beilstein Institute for Organic Chemistry, BRN 2024248, XP002284533.
Database Beilstein 'Online!, Beilstein Institute for Organic Chemistry, BRN 2033596, XP002284534.
Database Beilstein 'Online!, Beilstein Institute for Organic Chemistry, BRN 2064766, XP002284535.
Database Beilstein 'Online!, Beilstein Institute for Organic Chemistry, BRN 2065735, XP002284536.
Database Beilstein 'Online!, Beilstein Institute for Organic Chemistry, BRN 8881860, XP002284537.
Djerassi et al., "Mass Spectrometry in Structural and Stereochemical Problems. LXV. Synthesis and Fragmentation Behaviour of 15-Keto steroids", *Journal of the American Chemical Society*, 87(4):817-826 (1965).
Gao et al., "A Novel Method for the Synthesis of a C/D-Ring Synthon of Vitamin D Derivatives From Hyodeoxycholic Acid", *Tetrahedron Letters*, 40(1):131-132 (1999).
Kasal, "Epalons: 6-Substituted Derivatives of 7-Norepiallopregnanolone", *Tetrahedron*, 56(22):3559-3565 (2000).
Lardy et al., "Ergosteroids II: Biologically Active Metabolites and Synthetic Derivatives of Dehydroepiandrosterone", *Steroids: Structure, Function and Regulation*, 63(3):158-165 (1998).
Liebermann et al., "D5-Cholestene-3b, 4b, 7a-triol and the Inhibition of the Oxidation of Hydroxyl Groups by Vicinal Substituents", *Journal of the American Chemical Society*, 72:5211-5218 (1950).
McMorris et al., "Structures of Oogoniol-1, -2, and -3, Steroidal Sex Hormones of the Water Mold", *Journal of the American Chemical Society*, 97(9):2544-2545 (1975).
Miller et al., "A Ruthenium Catalyzed Osxidation of Steroidal Alkenes to Enones", *Tetrahedron Letters*, 37(20):3429-3432 (1996).
Nace et al., "Novel Products from the Oxidation of d5 Steroids with Potassium Permanganate in Pyridine", *Journal of Organic Chemistry*, 35:3846-3851 (1970).
Ockels et al., "Darstellung Von Spezifisch Deuterium-Markierten Analogen Des Androst-5-En-3Beta-Ol, 3Beta-Ol, 3Beta-Ol", *Tetrahedron*, 32(1):135-142 (1976).
Teng et al., "Sterol Metabolism. XX. Cholesterol 7b-Hydroperoxide", *Journal of Organic Chemistry*, 38:119-123 (1973).
Witiak et al., "Inhibitors and Stimulators of Cholesterolgenesis Enzymes", *Journal of Medicinal Chemistry*, 14(8):684-693 (1971).
Clinton et al., "D-Homosteroids. I. Derivatives of D-Homoetiocholan-3βa-ol-11,17a-dione", *Journal of the American Chemical Society*, 79:6475-6480 (1957).
Database Beilstein, Beilstein Institute for Organic Chemistry, Frankfurt-Main, DE; BRN 2606100, XP002295651 (Abstract).
DeMarcano et al., "D-Homoandrostanes.2.Preparation and Properties of some Dioxygenated D-Homo-5a-Androstanes", *Journal of Organic Chemistry*, 42(7):1221-1225 (1977).
DeMarcano et al.,"D-Homoandrostanes.4.The Incubation of some D-Homo-5a-Androstanes with Rhizopus Nigricans", *Steroids*, 41(1):1-13 (1983).
Eadon et al., "Synthesis and Biological Activity of D-Bishomo Steroids", *Journal of Medicinal Chemistry*, 15(1):89-91 (1972).
Girdhar et al., "Highly Efficient Lewis Acid Catalyzed, One Step Conversions of 16alpha, 17alpha-epoxy-3beta-hydroxypregn-5-en-20-one to d-homosteroid and DELTA<13>-Steroids", *Tetrahedron*, 57(33):7199-7204 (2001).
Seto et al., "Synthesis and Biological Activity of 6a-Carbabrassinolide: B-Ring Homologation of 6-Oxo-Steroid to 6-Oxo-7a-Homosteroid with Trimethylsilyldiazomethane-Boron Trifluoride Etherate", *Tetrahedron Letters*, 40(12):2359-2362 (1999).
English language translation of Kuritzkes et al., "3-epi-Uzarigenin and 3-epa-17α-Uzarigenin", Helvetica Chimica Acta, 14:1502-1515 (1959).
English language translation of Ockels et al., "Darstellung Von Spezifisch Deuterium-Markierten Analogen Des Androst-5-En-3Beta-Ol", 3Beta-Ol, 3Beta-Ol, Tetrahedron, 32(1):135-142 (1976).
English language translation of Polonia et al., "Die Konstitution des Xysmalogenins", Helvetica Chimica Acta, 11:1437-1446 (1959).
English language translation of Tamm et al., "Umwandlung von Cardenoliden durch Mikroorganismen. III. Umsetzung von Aglykonen und Glykosiden mit *Fusarium lini*", Helvetica Chimica Acta, 21: 239-259 (1959).
English language translation of Tschesche et al., "Uber pflanzliche Herzgifte, XIX. Mitteil., Die Glykoside der Uzara-Wurzel", *Chemische Berichte*, 85th vol., No. 11:1042-1053 (1952).
Huang et al., "Synthesis of Cholesterol and Its Analog with Fluorinated Side-Chains", *Journal of Fluorine Chemistry*, 43:305-318 (1988).
Kihira et al., "Synthesis of Sulfonate Analogs of Bile Acids", *Steroids*, 57:193-198 (1992).
McKee et al., "HIV-Inhibitory Natural Products. 11. Comparitive Studies of Sulfated Sterols from Marine Invertabrates", *J. Med. Chem.*, 37:793-797 (1994).
Riccio et al., "Unusual Sulfated Marine Steroids from the Ophiuroid *Ophioderma Longicaudum*", *Tetrahedron*, 41(24):6041-6046 (1985).

(56) References Cited

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).

Vippagunta et al. (Advanced Drug Delivery Reviews, 48 (2001), pp. 3-26).

Feng et al. "Triterpenoids from the Mangrove Plant *Hibiscus tiliaceus*" *Helvetica Chimica Acta*, 91: 850-855 (2008).

Iorizzi, M. et al. "Investigation of the polar steroids from an Antarctic starfish of the family echinasteridae: isolation of twenty seven polyhydroxysteroids and steroidal oligoglycosides, structures and biological activities"; Tetrahedron (1996), vol. 52(33), pp. 10997-11012 See Abstract; Compound 25 and Compound 26.

Kuramoto, T. et al. "Chemical synthesis of 5 β—cholestane-3a,7a,24,25-tetrol and its metabolism in the perfused rabbit liver"; J. of Biol. chem. (1978), vol. 253(13), pp. 4688-4692 See Abstract and Fig. 1.

Iorizzi, M. "Polyoxygenated marine steroids from the deep water starfish *Styracaster caroli*"; Journal of Natural Products (1994), vol. 57(10), pp. 1361-1373.

\* cited by examiner

LIVER X RECEPTOR AGONISTS

RELATED APPLICATION

This application claims priority of U.S. Provisional Application No. 61/229,386, filed on Jul. 29, 2009. The prior application is incorporated by reference in its entirety.

BACKGROUND OF THE INVENTION

Liver X receptors (LXRs), members of the nuclear receptor super-family, regulate expression of genes relating to cholesterol metabolism and homeostasis. Two LXR isoforms, i.e., LXRα and LXRβ, have been identified. While LXRα expression is restricted to liver, kidney, intestine, fat tissue, macrophages, lung, and spleen, LXRβ is expressed in almost all tissues and organs.

LXRs modulate lipid metabolism and ApoE gene expression. Accumulation of lipids in arteries causes atherosclerosis and accumulation of lipids in the cornea results in corneal arcus. See, e.g., Zech et al., Lipids in Health and Disease 2008, 7:7. Deficiency of ApoE gene expression attributes to diseases such as Alzheimer's disease. See, e.g., Artiga et al., Human Molecular Genetics 1998, 7: 1887. Thus, LXR agonists can be used to treat atherosclerosis, corneal arcus, and Alzheimer's disease.

LXRs also stimulate insulin secretion and inhibit inflammation and autoimmune reactions. See Jamroz-Wiśniewska et al., Postepy Hig Med. Dosw. 2007, 61:760. Thus, LXR agonists can be used to treat diabetes (e.g., Type 1 diabetes) and inflammatory/autoimmune disorders.

Further, it has been found that activation of LXRs leads to inhibition of the hedgehog signaling pathway, which plays a key role in developing cancer in various organs (e.g., brain, lung, blood, prostate, breast, and skin) See, e.g., Watkin et al., Nature, 2003, 442: 313-317. Thus, LXR agonists can also be used to treat cancer. See, e.g., Chu et al., Journal of biomedical science, 2007, 14(5): 543-553.

SUMMARY OF THE INVENTION

The present invention is based on the discovery of very effective LXR agonists.

One aspect of this invention relates to compounds of formula (I):

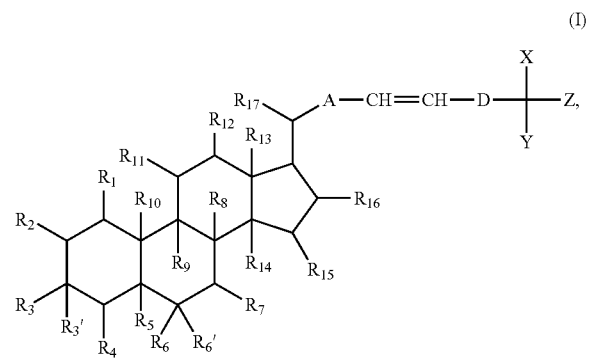

(I)

in which each of $R_1$, $R_2$, $R_4$, $R_5$, $R_7$, $R_{11}$, $R_{12}$, $R_{15}$, $R_{16}$, and $R_{17}$, independently, is hydrogen, halo, alkyl, hydroxyl, amino, carboxyl, or sulfonic acid; each of $R_3$, $R_{3'}$, $R_6$, and $R_{6'}$, independently, is hydrogen, halo, alkyl, hydroxyl, amino, carboxyl, or sulfonic acid, or $R_3$ and $R_{3'}$ together or $R_6$ and $R_{6'}$ together are =O; each of $R_8$, $R_9$, $R_{10}$, $R_{13}$, and $R_{14}$, independently, is hydrogen, halo, alkyl, hydroxyalkyl, alkoxy, hydroxyl, or amino; each of A and D, independently, is deleted or alkylene; X and Y, independently, is alkyl; and Z is hydroxyl or alkoxy.

Referring to formula (I), one subset of the compounds has one or more of the following features: each of X and Y is haloalkyl (e.g., $CF_3$); Z is hydroxyl, each of $R_3$ and $R_6$ is OH, and each of $R_{3'}$ and $R_{6'}$ is H; each of $R_1$, $R_2$, $R_4$, $R_5$, $R_7$, $R_8$, $R_9$, $R_{11}$, $R_{12}$, $R_{14}$, $R_{15}$, $R_{16}$, and $R_{17}$, independently, is hydrogen, halo, alkyl, hydroxyl, or amino (e.g., each of them is hydrogen); each of $R_{10}$ and $R_{13}$, independently, is hydrogen or alkyl (e.g., each of them is methyl); and both A and D are deleted, A is $CH_2$ and D is deleted, or A is deleted and D is $CH_2$.

Referring to formula (I), another subset of the compounds has one or more of the following features: each of X and Y is haloalkyl (e.g., $CF_3$); Z is hydroxyl; $R_3$ and $R_{3'}$ together are =O, $R_6$ is OH, and $R_{6'}$ is H; each of $R_1$, $R_2$, $R_4$, $R_5$, $R_7$, $R_8$, $R_9$, $R_{11}$, $R_{12}$, $R_{14}$, $R_{15}$, $R_{16}$, and $R_{17}$, independently, is hydrogen, halo, alkyl, hydroxyl, or amino (e.g., each of them is hydrogen); each of $R_{10}$ and $R_{13}$, independently, is hydrogen or alkyl (e.g., each of them is methyl); and both A and D are deleted, A is $CH_2$ and D is deleted, or A is deleted and D is $CH_2$.

Referring to formula (I), a further subset of the compounds has one or more of the following features: each of X and Y is haloalkyl (e.g., $CF_3$); Z is hydroxyl; $R_6$ and $R_{6'}$ together are =O, $R_3$ is OH, and $R_{3'}$ is H; each of $R_1$, $R_2$, $R_4$, $R_5$, $R_7$, $R_8$, $R_9$, $R_{11}$, $R_{12}$, $R_{14}$, $R_{15}$, $R_{16}$, and $R_{17}$, independently, is hydrogen, halo, alkyl, hydroxyl, or amino (e.g., each of them is hydrogen); each of $R_{10}$ and $R_{13}$, independently, is hydrogen or alkyl (e.g., each of them is methyl); and both A and D are deleted, A is $CH_2$ and D is deleted, or A is deleted and D is $CH_2$.

The term "alkyl," the prefix "alk" (e.g., as in alkoxy), and the suffix "-alkyl" (e.g., as in hydroxyalkyl and haloalkyl) mentioned above all refer to mono-valent $C_{1-18}$ linear or branched hydrocarbon, which is optionally substituted with halo, hydroxyl, or carboxyl, and optionally inserted with —NH—, —N(alkyl)-, —O—, —S—, —SO—, —SO$_2$—, —O—SO$_2$—, —SO$_2$—O—, —SO$_3$—O—, —CO—, —CO—O—, —O—CO—, —CO—NR'—, or —NR'—CO—.

The term "alkylene" refers to bi-valent $C_{1-18}$ linear or branched hydrocarbon (e.g., —$CH_2$—).

Examples of the cholesterol compounds of this invention are shown below:

Compound 1

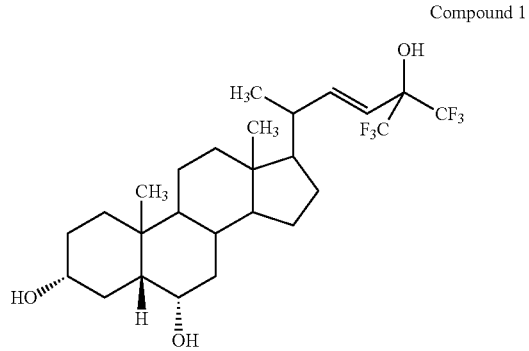

Compound 2

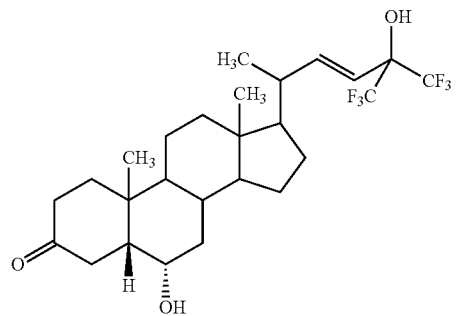

Compound 3

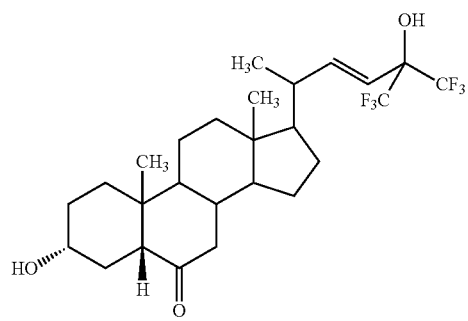

Compound 4

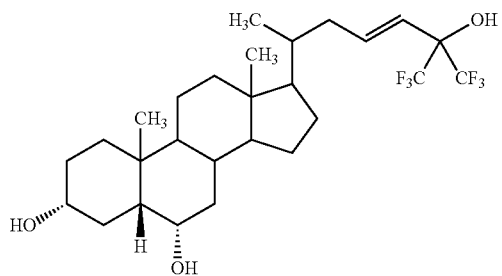

The compounds described above also include their salts and prodrugs, if applicable. Such salts, for example, can be formed between a positively charged substituent in a compound of this invention (e.g., amino) and an anion. Suitable anions include, but are not limited to, chloride, bromide, iodide, sulfate, nitrate, phosphate, citrate, methanesulfonate, trifluoroacetate, and acetate. Likewise, a negatively charged substituent in a compound of this invention (e.g., carboxylate) can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing steroid compounds described above.

Another aspect of this invention relates to a pharmaceutical composition including an effective amount of a compound of this invention and a pharmaceutically acceptable carrier. Also within the scope of this invention are methods of using such a compound to lower the cholesterol level in blood and treat an LXR-mediated disease such as atherosclerosis, diabetes, Alzheimer's disease, corneal arcus, an inflammatory disorder, and cancer, and use of such a compound to manufacture a medicament used in lowering the cholesterol level and treating one of these diseases.

Details of several compounds of this invention are set forth in the accompanying description below. Other features, objects, and advantages of this invention will be apparent from the description and from the claims.

DETAILED DESCRIPTION OF THE INVENTION

Compounds of this invention can be prepared using a suitable known steroid compound as a starting material. Examples of known steroid compounds include cholic acid, dehydrocholic acid, deoxycholic acid, lithocholic acid, ursodeoxycholic acid, hyocholic acid, hyodeoxycholic acid, and cholanoic acid. They are either commercially available or can be synthesized by methods described in the literature, e.g., Roda et al., F. *Lipid Res.*, 1994, 35: 2268-2279; and Roda et al., *Dig. Dis. Sci.*, 1987, 34: 24S-35S. These steroid compounds can be converted to the compounds of this invention via well known methods. For example, certain compounds of this invention can be prepared from commercially available hyodeoxycholic acid (3α,6α-dihydroxy-5β-cholan-24-oic acid, Sigma, St. Louis, Mo.). As shown in Scheme 1 below, protected hyodeoxycholic acid is subjected to α-selenylation. The obtained selenyl product is oxidized to form α,β-unsaturated ester, which is then reduced by di(iso-butyryl)alumina hydride to form an aldehyde compound. The aldehyde is converted to an alcohol compound by reacting with trimethyl (trifluoromethyl)silane. See, e.g., U.S. Pat. No. 7,012,069. The alcohol then undergoes the Dess-Martin reaction to form ketone compound. See Dess et al., J. Org. Chem., 1983, 38: 4155. The ketone is treated with trimethyl(trifluoromethyl) silane again to afford an alcohol, α-substituted with two trifluoromethyl groups.

Scheme 1

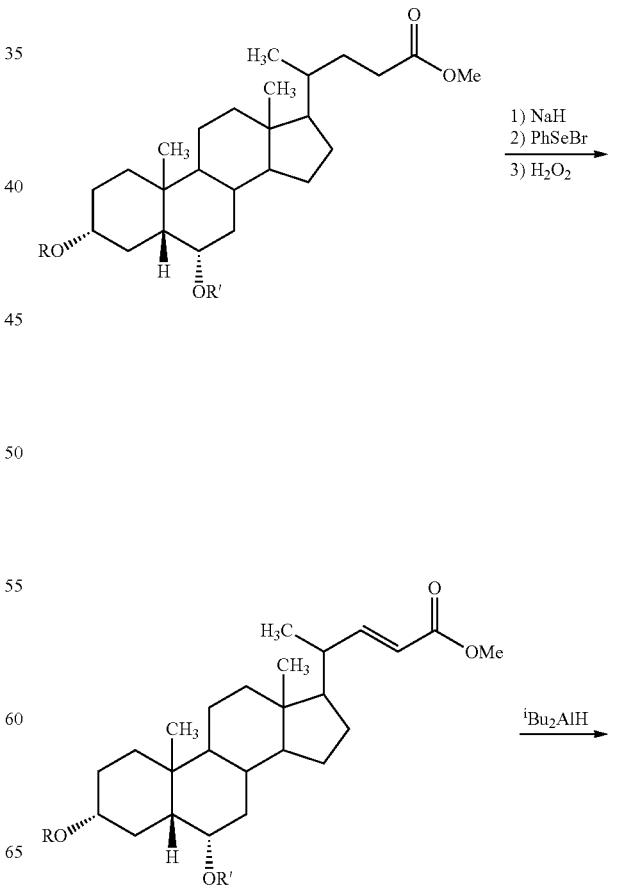

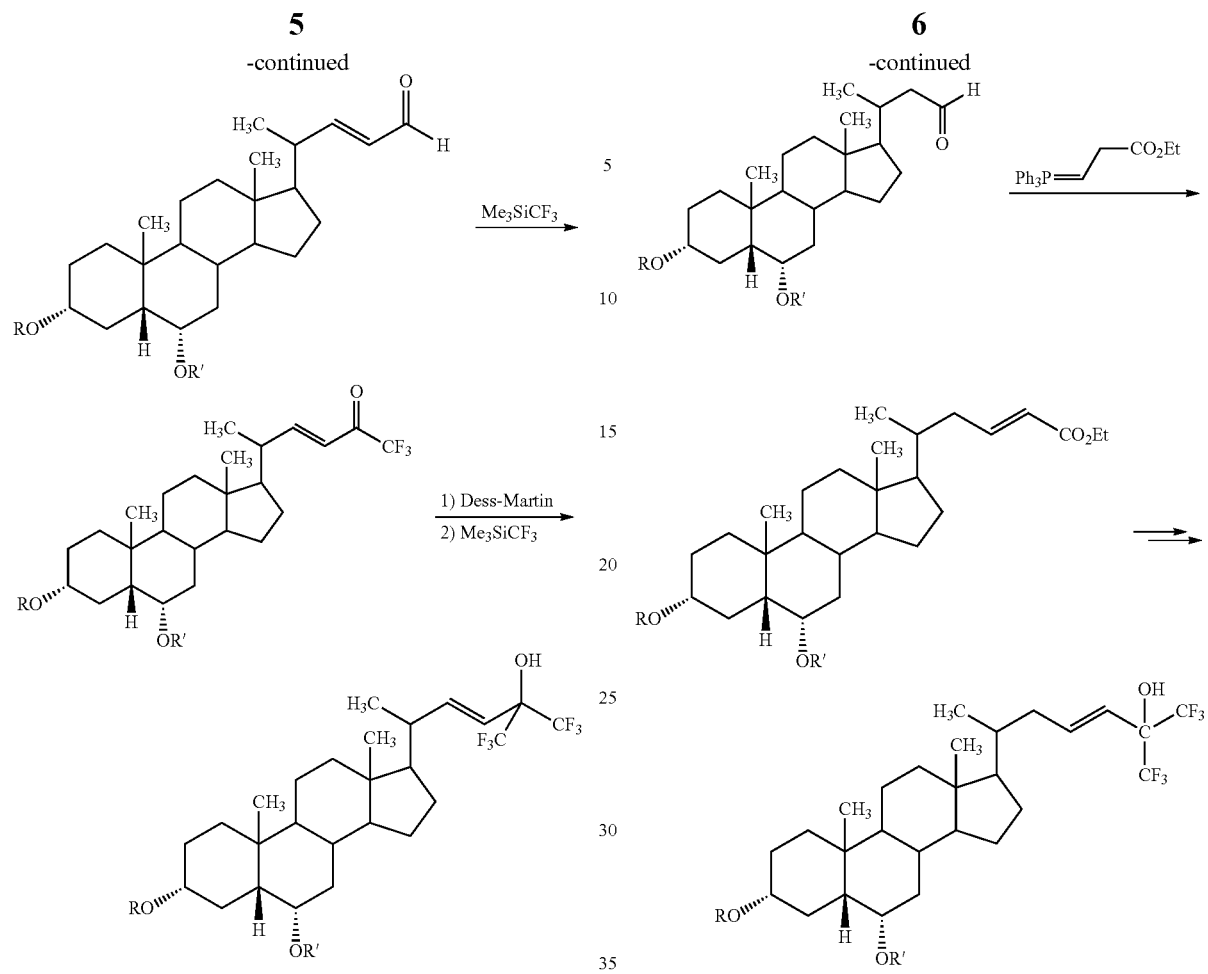

The α,β-unsaturated ester prepared in the above synthetic route can also be used to synthesize other compounds of this invention. See Scheme 2 below:

As shown above, the α,β-unsaturated ester is oxidized to afford an α,β-epoxide ester, which is decarboxylated under an acid condition and converted to aldehyde. The aldehyde is subjected to the Wittig reaction to provide α,β-unsaturated ester, which additionally contains a methylene moiety compared to the starting material. This α,β-unsaturated ester is converted to a compound of this invention (shown above) by the method similar to that used in Scheme 1.

Scheme 3 below illustrates another synthetic route to compounds of this invention. Briefly, hyodeoxycholic acid is converted via cleavage oxidation to an alkene compound, which is reacted with another alkene compound via olefin metathesis reaction in the presence of Grubb's catalyst.

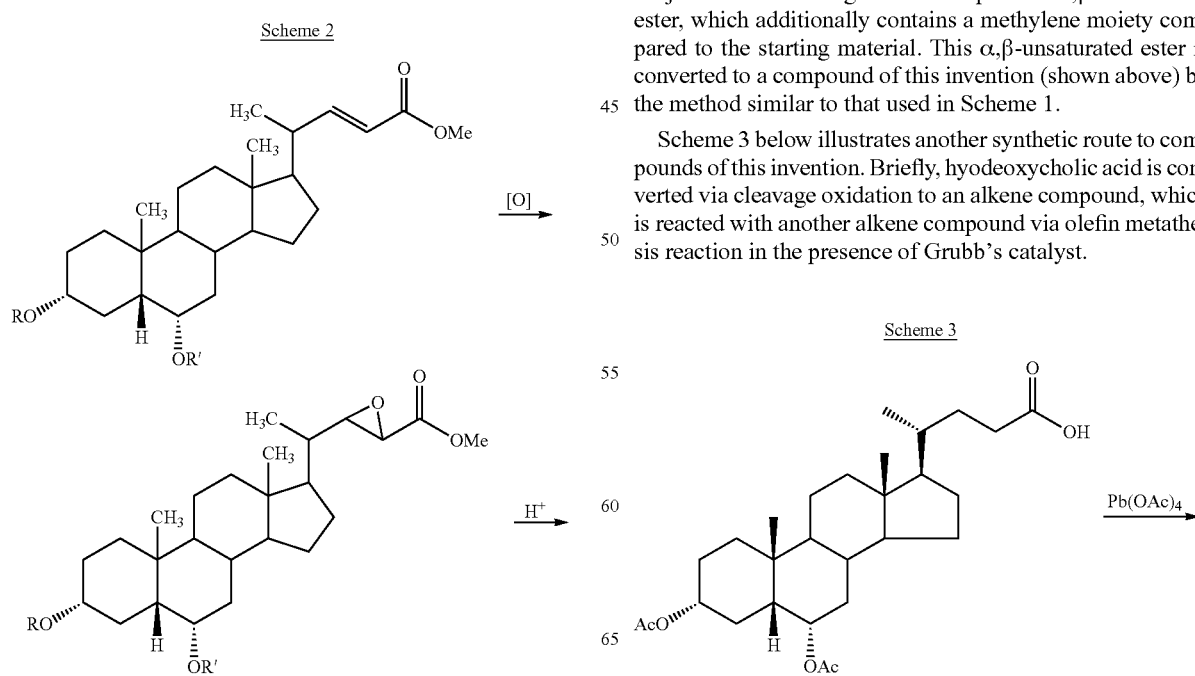

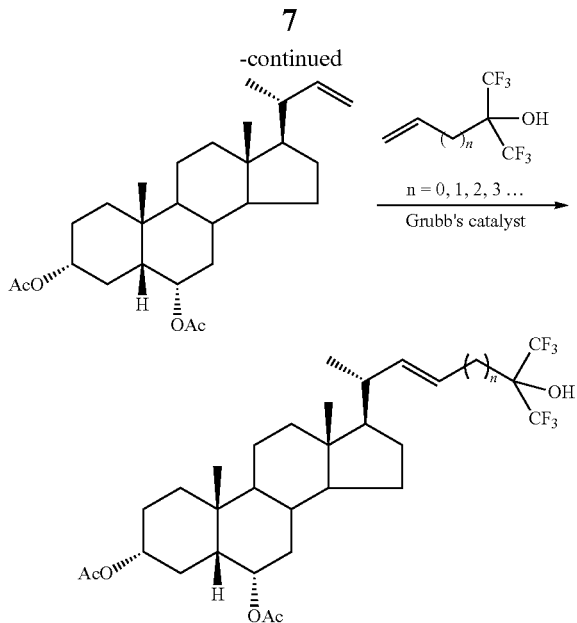

The methods described above may be modified to prepare other cholesterol compounds of this invention. For instance, the 3- or 6-hydroxyl group of Compound 1 is partially oxidized to afford Compounds 2 and 3, which respectively have an oxo group at the 3- or 6-position. The methods may also include steps to add or remove suitable protecting groups in order to ultimately allow synthesis of the cholesterol compounds of this invention. In addition, synthetic steps may be performed in an alternative sequence or order to give the desired compounds. Synthetic chemistry transformations and protecting group methodologies (protection and deprotection) useful in synthesizing applicable cholesterol compounds are known in the art and include, for example, those described in R. Larock, *Comprehensive Organic Transformations*, VCH Publishers (1989); T. W. Greene and P.G.M. Wuts, *Protective Groups in Organic Synthesis*, 2$^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds of this invention are LXR agonists and can be used to treat LXR-mediated diseases, such as atherosclerosis, diabetes (e.g., Type 1 diabetes), Alzheimer's disease, corneal arcus, inflammatory/autoimmune disorders, and cancer. Thus, this invention relates to a method of treating a LXR-mediated disease by administering to a subject an effective amount of one of the cholesterol compounds described above. The term "treating" or "treatment" refers to administering an active compound to a subject, who has a LXR-mediated disease, a symptom of such a disease, or a predisposition toward such a disease, with the purpose of conferring a therapeutic effect, e.g., to cure, relieve, alter, affect, ameliorate, or prevent the above-described disease, the symptom of it, or the predisposition toward it. "An effective amount" refers to the amount of the compound which is required to confer therapeutic effect on the treated subject. The interrelationship of dosages for animals and humans (based on milligrams per square meter of body surface) is described by Freireich et al., Cancer Chemother. Rep. 1966, 50, 219. Effective doses will vary, as recognized by those skilled in the art, depending on the route of administration, the excipient usage, and the optional co-usage with other therapeutic treatments.

The term "cancer" refers to diseases in which certain cells display uncontrolled growth, invasion, and/or metastasis. Examples of cancer include, but are not limited to prostate cancer, breast cancer, skin cancer, brain cancer, lung cancer, and leukemia.

Inflammatory diseases that can be treated by the method of this invention include, but are not limited to, asthma, atherosclerosis, rheumatoid arthritis, inflammatory bowel diseases, Crohn's disease, ulcerative colitis, ischemic heart disease, cardiomyopathy, glomerulonephritis, nephritic syndrome, hepatitis C infection, and respiratory syncytial virus infection (pulmonary).

Autoimmune diseases that can be treated by the method of this invention include, but are not limited to, allergic encephalopathy, chronic obstructive pulmonary disease, psoriasis, psoriatic arthritis, systemic lupus erythematosus, and multiple sclerosis.

To practice the method of the present invention, a composition having one or more cholesterol compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active cholesterol compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

The cholesterol compounds described above can be preliminarily screened for their efficacy in acting as LXR agonists by an in vitro assay (see Example 2 below) and then confirmed by an in vivo assay using an animal model, e.g., mice having a LXR-mediated disease (see Examples 3 and 4 below). Other methods will also be apparent to those of ordinary skill in the art. The dosage useful for treating the LXR-mediated disease can be determined based on the result of the in vivo assay.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Chemical Synthesis (A) Preparation of Methylation of Hyodeoxycholic Acid

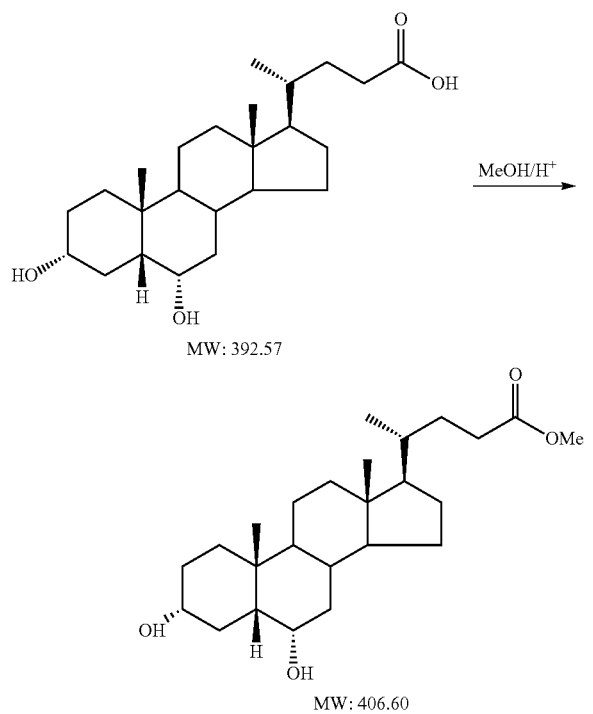

To a solution of starting material (162 g, 0.41 mole) in 1.0 L of methanol was added 10 ml of conc. $H_2SO_4$. The mixture was stirred at room temperature for 4 hours. TLC indicated completeness of the reaction. The reaction solution was then neutralized with saturated $NaHCO_3$ and evaporated to remove the solvent. The remaining residue was diluted with ethyl acetate, washed with water and brine, and dried over $Na_2SO_4$. The solvent was concentrated to afford 168 g (100%) of crude methyl ester, which was directly used for the next step.

(B) Protection of the Hydroxyl Group with Tert-Butyldimethylsilyl Chloride

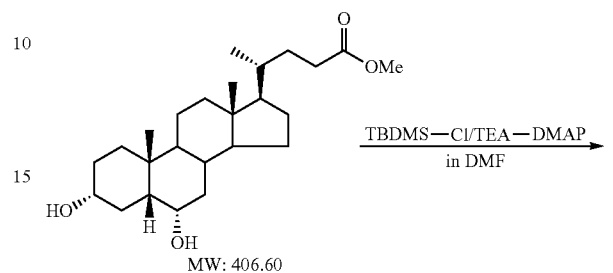

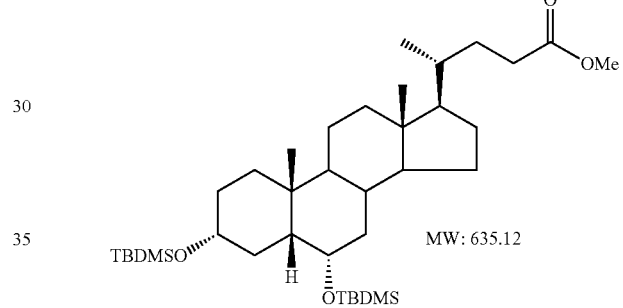

To a solution of crude methyl ester from the above reaction (165 g, 0.40 mole) in 1.0 L of DMF was added triethylamine (170 mL, 1.2 mole), DMAP (4.95 g, 3% w/w), and TBDMS-Cl (121 g, 0.80 mole). The reaction mixture was stirred at 40° C. overnight. TLC indicated completeness of the reaction. After most of the DMF was removed by evaporation, the residue was dissolved in 2.0 L of ethyl acetate and then washed with water three times (1.5 L, 1.0 L, 500 ml). The aqueous layers were combined and extracted with 1.0 L of ethyl acetate. The extraction layer was washed with water twice (300 ml, 100 ml). The organic layers were combined and dried over $Na_2SO_4$. Evaporation of the solvent afforded 253 g of the crude product, which was purified by flash column chromatography to give 221 g (87%) of pure TBDMS protected product.

(C) Preparation of α-Selenide

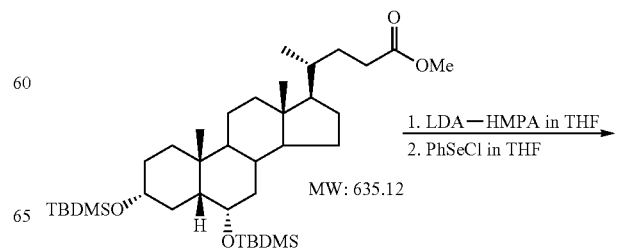

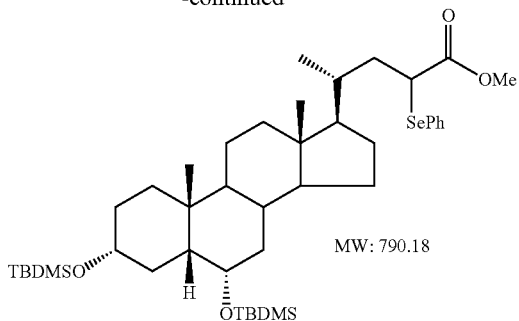

The above TBDMS protected compound (172 g, 0.27 mole) was dissolved in 870 mL of anhydrous THF. 48 mL of HMPA (0.27 mole) was added. The reaction mixture was cooled to −72° C. in an acetone/dry ice bath. LDA (1.5 M in hexane, 365 mL, 0.55 mole) was added dropwise to the solution. The mixture was further stirred for 1 h at −72° C., followed by addition of PhSeCl (78 g, 0.4 mole) in THF (anhydrous, 230 mL) over 1 h. The reaction mixture was warmed up to room temperature and allowed to stand overnight. After the reaction was completed, it was quenched with saturated NH₄Cl solution (200 ml). The organic phase was removed and washed with water 100 ml×3. The aqueous phase was extracted with ethyl acetate (200 ml). The combined organic layer was dried over Na₂SO₄ and then concentrated in vacuo to give oily residue, which was purified by silica gel column chromatography (ethyl acetate/hexane, from 1:100 to 1:30). The product was obtained as a yellow solid (130.5 g, yield: 61%).

(D) Selenoxide Oxidation

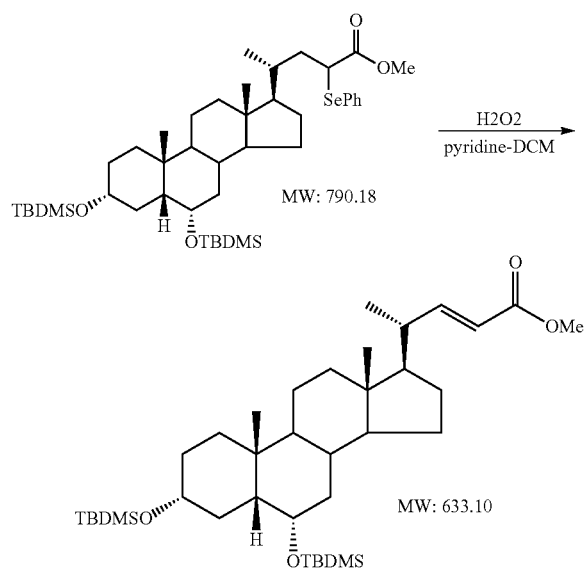

The α-phenylselenyl compound (120 g, 0.15 mole) was dissolved in dichloromethane (800 mL). After 24 mL of pyridine (0.30 mole) was added, hydrogen peroxide (35 w/w % solution in water, 36 g, 0.37 mole) in 120 mL water was slowly added to the solution at room temperature. The resulting mixture was stirred for 1 h at 30-35° C. After reaction was completed, the reaction solution was quenched by saturated NaHCO₃ (140 mL). The aqueous phase was extracted with dichloromethane twice (200 ml, 100 ml). The combined organic phase was washed with water (200 ml×2), dried over Na₂SO₄, and then concentrated. The residue was purified by silica gel column chromatography (ethyl acetate/hexane, from 1:100 to 1:30). The product was obtained as a light yellow solid (88 g, yield 93%).

(E) DIBAL Reduction of Methyl Ester

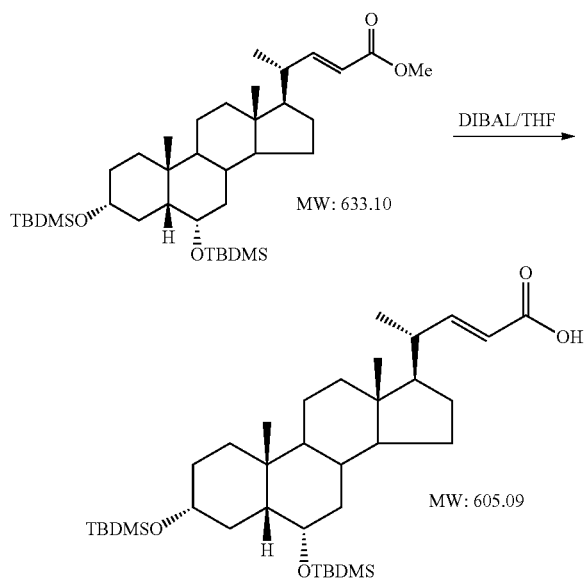

70 g of methyl ester (0.11 mole) were dissolved in 150 mL of anhydrous THF. After the mixture was cooled down to −78° C. in an acetone/dry ice bath, 293 mL of 1.5 M DIBAL/toluene solutions were added dropwise. The resulting mixture was stirred 1 h at −78° C. and then, warmed up to room temperature for another 2 hours. 500 mL of 5M ammonium chloride solution were slowly added to quench the reaction. The organic layer was separated, washed with water twice, dried over Na₂SO₄, and concentrated to give 54 g (81%) of the crude alcohol product, which was directly used for the next step reaction.

(F) Oxidation of Alcohol to Aldehyde

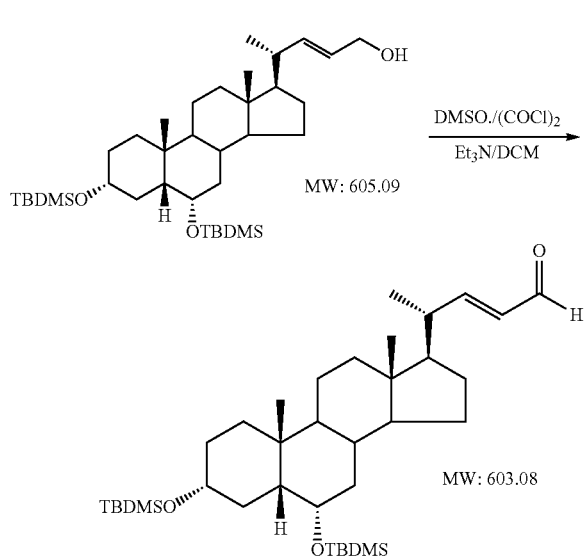

54 g of alcohol were added to 1 L of dry CH₂Cl₂ under a nitrogen atmosphere. After the mixture was cooled to −50° C., DMSO (52 ml) was added dropwise. Then oxalyl chloride (31 mL) was added. The reaction mixture was stirred at −50° C. for 0.5 h, then triethylamine (127 mL) was added and the resulting mixture was stirred at 0-25° C. for 1 h. A saturated NH₄Cl solution (2 L) was added to quench the reaction. After stirring for another 15 min., more CH₂Cl₂ was added to extract the product. The organic phase was washed with sat. NaHCO₃ and then brine, dried over Na₂SO₄, and concentrated. The resulting residue was then subjected to column chromatography purification, giving the aldehyde product 39 g (72%).

(G) Reaction of Aldehyde with Trifluoromethyltrimethylsilane

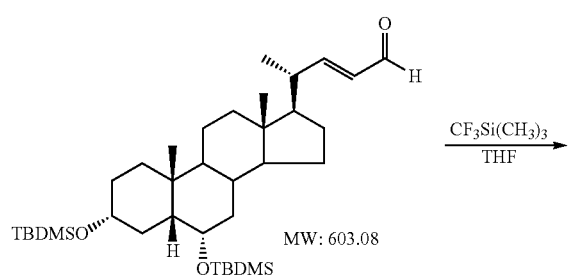

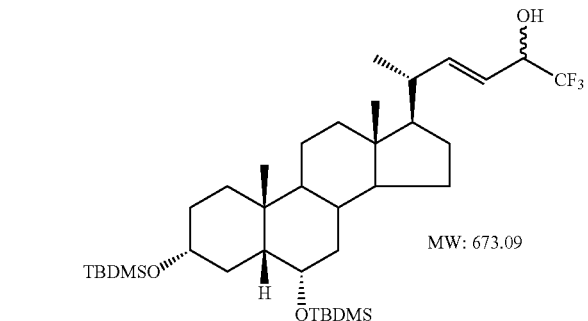

Under nitrogen atmosphere, 33.2 g (55 mmole) of aldehyde were dissolved in 390 mL of THF. After 200 mg of CsF were added and stirred for 10 minutes, 9.39 g (66 mmole) of CF₃Si(CH₃)₃ were added dropwise. After the resulting mixture was stirred overnight, the solvent was removed under reduced pressure. The residue was dissolved in ethyl acetate (300 mL), washed with 5% NaHCO₃ and brine, dried over Na₂SO₄, and concentrated. The residue was purified by short column chromatography to give 26 g (70%) of the trifluoromethyl product.

(H) Oxidation of Trifluoromethyl-alcohol to Trifluoro-ketone

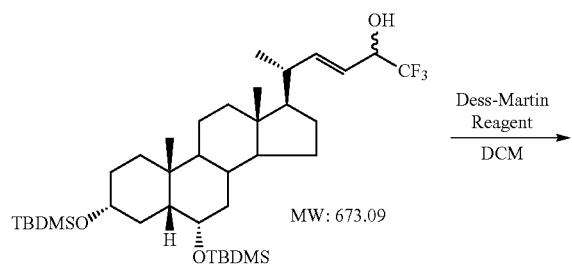

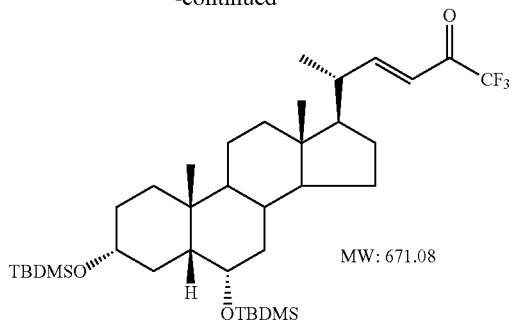

Under nitrogen atmosphere, 16.67 g (39.3 mmole) of Dess-Martin reagent were added to a solution of trifluoromethyl compound 24 g (35.7 mmole) in 300 mL of anhydrous CH₂Cl₂. The reaction mixture was stirred at room temperature overnight. 500 mL of ethyl ether were added and a lot of solid was precipitated. The solid was filtered and washed with ethyl ether. The combined organic phase was washed with saturated NaHCO₃ and then brine, dried over Na₂SO₄, and concentrated in vacuo to give a residue, which was purified by column chromatography to give 21.1 g (80%) of trifluoromethyl-ketone product.

(I) Reaction of Trifluoromethyl-Ketone with Trifluoromethyltrimethylsilane

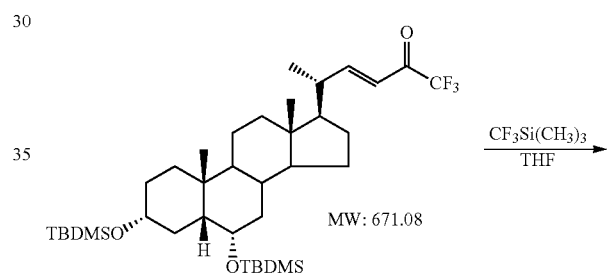

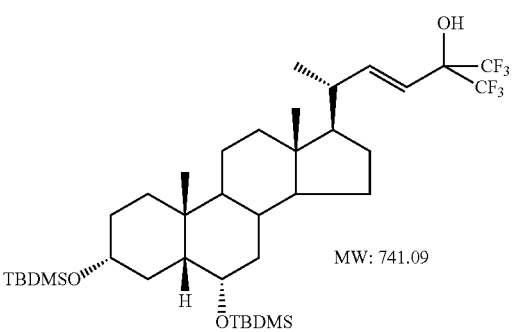

Under nitrogen atmosphere, 20 g (29.8 mmole) of trifluoro ketone were dissolved in 250 mL of THF. After 150 mg of CsF were added and stirred for 10 minutes, 5.09 g (35.8 mmole) of CF₃Si(CH₃)₃ were added dropwise. The resulting mixture was stirred overnight, and the solvent was removed under reduced pressure. The residue was dissolved in ethyl acetate (200 mL), washed with 5% NaHCO₃ and brine, dried over Na₂SO₄, concentrated under reduced pressure. The residue was partially purified by short column chromatography to give 15.9 g (72%) of di-trifluoromethyl product.

(J) Removal of the TBDMS Protecting Group to Compound 1

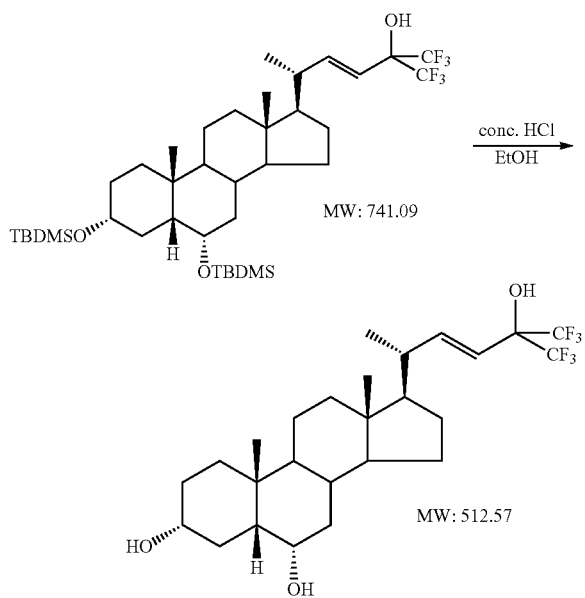

15.9 g (21.5 mmole) of di-trifluoromethyl compound were dissolved in 100 mL of ethanol. 1 mL conc. HCl was added. The mixture was stirred at room temperature for 2 h. 1 mL of 12 N NaOH was added and the mixture was concentrated to remove most of the ethanol. 100 mL ethyl acetate and 30 mL water were added. The organic layer was separated, washed with water, dried over $Na_2SO_4$, and concentrated to give a residue, which was then purified by column chromatography. The product was further crystallized from ether. 9.7 g (88%) of pure Compound 1 was obtained and the structure of the product was confirmed by NMR analysis.

(K) Oxidative Cleavage of Carboxylic Acid

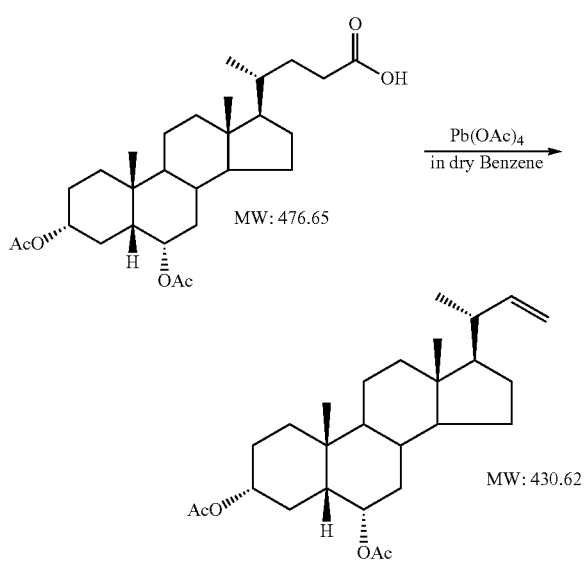

To a solution of starting material (500 g) in 2.5 L of dry benzene were added 30 g of cuprous acetate and 32 mL of dry pyridine. The reaction mixture was warmed up to 75° C. 920 g of lead(VI) acetate were added slowly. The resulting mixture was refluxed overnight. After filtration and washing the solids with benzene, most benzene was evaporated under reduced pressure. The residue was purified by column chromatography twice to give 35.4 g of the pure product.

Example 2

Reporter Gene Assay

The ability of Compound 1 to act as an LXR agonist was tested using a luciferase-based reporter gene assay according to the method described in Graham et al., Virology, 1973, 52:456. The assay is described below:

Wells of a 48-well plate were seeded with 50,000 human embryonic kidney (HEK293) cells in 0.25 mL of Dulbecco's modified Eagle's media containing 10% charcoal-stripped fetal bovine serum (DMEM+10% CS-FBS). HEK293 cells were co-transfected with various plasmid DNAs using a calcium phosphate co-precipitation method (Graham et al., Virology, 1973, 52:456). To each well was added 0.25 mL of a transfection mix (1.36 mL transfection components and 11.5 mL DMEM+10% CS-FBS) containing 60 ng of a firefly luciferase-based reporter plasmid, 60 ng of pSG5 containing human LXRα or LXRβ cDNA, 0.6 ng of the sea pansy luciferase normalization plasmid phRL-TK (Promega), and 220 ng of pBS/SK+II. The firefly luciferase-based reporter plasmid consisted of four copies of an LXR DR-4 response element, each copy containing the sequence AGGTCACAG-GAGGTCA upstream of the c-fos minimal promoter (−56 to +109) inserted into the Sma I site of the plasmid pGL3-Basic containing the firefly luciferase gene (Promega, Madison, Wis.). After 5 hours, the transfection mix was removed and replaced with DMEM+10% CS-FBS containing a test compound at various concentrations. After 48 hours, the media was removed and the cells were lysed using 0.1 mL of passive lysis buffer (Promega). Firefly and sea pansy luciferase activities in the lysate were measured using a dual luciferase assay (Promega) and a Monolight luminometer. Firely luciferase activity was normalized to sea pansy luciferase activity in each sample. Fold activation of the firefly luciferase reporter plasmid was calculated from normalized relative light units in the presence and absence of the test compound.

The results show that Compound 1 was a very effective LXR agonist.

Example 3

Reduction of Cholesterol Level

Eight-week old male LDLR−/− mice on a C57BL/6 background (obtained from Jackson Laboratory) were fed an atherogenic diet (TD94059, Harlan TEKLAD, Madison, Wis.) for 8 weeks. During the same period, the mice received Compound 1 daily by gavage at a dose of 3 or 5 mg/kg in a microemulsion prepared by the method described in Gao et al., Int J Pharm 1998, 161:75-86). The control group (vehicle) received a microemulsion without Compound 1. After 8 weeks, the mice were fasted for 4 hours and anesthetized with ketamine (100 mg/kg) and xylazine (10 mg/kg). A blood sample was collected from the retro-orbital plexus of each mouse. 200 μl of plasma was fractionated on tandem Superose 6 fast protein liquid chromatography columns (Reardon et al., 2001). Cholesterol and triglyceride in the even-numbered fast protein liquid chromatography fractions and in plasma samples were measured using commercial kits (Stanbio Laboratory, Boerne, Tex.).

Analysis of the samples revealed a marked decrease the cholesterol and triglyceride levels in the blood in Compound 1-treated mice. It also shows that, at the dose of 3 mg/kg, Compound 1 reduced VLDL cholesterol and triglyceride levels, but not the HDL cholesterol level and at the dose of 5 mg/kg, it reduced the VLDL and LDL cholesterol and triglyceride levels, but not the HDL cholesterol level.

The mice were then perfused transcardially with PBS and then paraformaldehyde. The hearts and upper vasculatures were removed and prepared for histology as described in Reardon et al., *Arterioscler Thromb Vasc Biol* 2001, 21:1011-1016.

Lesions in the innominate artery were quantified using 4 digitally captured oil red O-stained 10 µm sections, separated by 100 µm and located 150-450 µm distal to the branch point of the innominate artery from the aortic arch. Lesions in the ascending thoracic aorta were assessed from three sections separated by 100 µm and located 100-300 µm below the apex of the lesser curvature of the aortic arch. Aortic sinus lesions were evaluated from 3 sections, separated by 100 µm and beginning at the site of appearance of the coronary artery. OpenLab software version 3.1.5 was used in the quantification.

In the innominate artery and ascending aorta arch, the atherosclerotic plaque sizes were significantly reduced in the mice treated with 5 mg/kg/day of Compound 1. In the aortic root, the mean atherosclerotic lesion area was significantly reduced in both mice treated with 3 mg/kg/day of Compound 1 and mice treated with 5 mg/kg/day of Compound 1.

Example 4

Prevention and Treatment of Type 1 Diabetes

This experiment is conducted to compare efficacy of Compound 1 and another steroid compound, i.e., 3α,6α,24-trihydroxy-24,24-di(trifluoromethyl)-5,3-cholane, in treating Type 1 diabetes.

Six-week old female non-obese diabetic mice are divided into 3 groups (10-12 mice each group). Two groups are respectively treated with 10 and 20 mg/kg/day of Compound 1 for 8 weeks. The third group is treated with 10 mg/kg/day of 3α,6α,24-trihydroxy-24,24-di(trifluoromethyl)-5,3-cholane also for 8 weeks. The plasma glucose levels are observed weekly from week 12 to week 34.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, conjugates structurally analogous to above-described conjugates also can be made, screened for the above-described activities and used to practice this invention. Thus, other embodiments are also within the claims.

What is claimed is:

1. A compound, wherein the compound is:

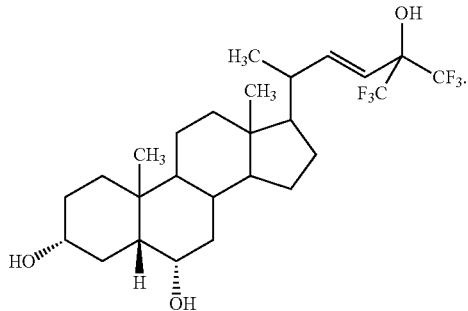 [SMILES: CC(/C=C/C(O)(C(F)(F)F)C(F)(F)F)C1CCC2C3C[C@H](O)[C@@H]4C[C@H](O)CCC4(C)C3CCC12C]

* * * * *